(12) United States Patent
Wiltz, Jr. et al.

(10) Patent No.: US 9,505,870 B2
(45) Date of Patent: *Nov. 29, 2016

(54) AMINE SUITABLE AS PU-CATALYST

(71) Applicant: HUNTSMAN PETROCHEMICAL LLC, The Woodlands, TX (US)

(72) Inventors: Eugene P Wiltz, Jr., The Woodlands, TX (US); Robert Allison Grigsby, Jr., Spring, TX (US); Jennifer Price, Humble, TX (US); Jingjun Zhou, The Woodlands, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/401,953

(22) PCT Filed: Apr. 23, 2013

(86) PCT No.: PCT/EP2013/058339
§ 371 (c)(1),
(2) Date: Nov. 18, 2014

(87) PCT Pub. No.: WO2013/182345
PCT Pub. Date: Dec. 12, 2013

(65) Prior Publication Data
US 2015/0152213 A1    Jun. 4, 2015

Related U.S. Application Data

(60) Provisional application No. 61/656,284, filed on Jun. 6, 2012.

(30) Foreign Application Priority Data

Jun. 19, 2012   (EP) ..................................... 12172577

(51) Int. Cl.
C08G 18/18     (2006.01)
C08G 18/76     (2006.01)
C08G 18/48     (2006.01)
C07C 217/04    (2006.01)
C07C 213/02    (2006.01)
C07C 217/08    (2006.01)
C07C 209/48    (2006.01)
C07C 253/30    (2006.01)

(52) U.S. Cl.
CPC ......... C08G 18/1833 (2013.01); C07C 209/48 (2013.01); C07C 213/02 (2013.01); C07C 217/04 (2013.01); C07C 217/08 (2013.01); C07C 253/30 (2013.01); C08G 18/48 (2013.01); C08G 18/7621 (2013.01)

(58) Field of Classification Search
None
See application file for complete search history.

(56) References Cited

U.S. PATENT DOCUMENTS 4,714,719 A    12/1987   Yamasaki et al.

FOREIGN PATENT DOCUMENTS

GB        1339931 A       12/1973
PL           94722   *    8/1977
WO   WO 2010/139521 A1 * 12/2010

* cited by examiner

*Primary Examiner* — Jeffrey Washville
(74) *Attorney, Agent, or Firm* — Huntsman International LLC

(57) ABSTRACT

An amine according to the invention has a formula $(CH_3)_2NCH_2CH_2OCH_2CH_2N(R1)(R2)$ wherein R1 is selected from $(CH_3)_2NCH_2CH_2OCH_2CH_2CH_2$— and R2 is selected from the group consisting of H—, $CH_3(C_nH_{2n})$—, $HO(C_mH_{2m})$— and $(CH_3)_2NCH_2CH_2OCH_2CH_2CH_2$—, n being an integer in the range of 0 to 5, m being an integer in the range of 2 to 4.

1 Claim, No Drawings

AMINE SUITABLE AS PU-CATALYST

CROSS-REFERENCE TO RELATED APPLICATIONS

This application is the National Phase of international Application PCT/EP2013/058339 filed Apr. 23, 2013 which designated the U.S. and which claims priority to E.P. Application Ser. No. 12172577.4 filed Jun. 19, 2012, and U.S. Application Ser. No. 61/656,284 filed Jun. 6, 2012. The noted applications are incorporated herein by reference.

The present invention relates to a new group of amines which are suitable for use as catalyst in the reaction of isocyanates with isocyanate reactive groups. The present invention further relates to a method to provide said amines Amines are well known as catalysts in the reaction of isocyanates with isocyanate reactive groups.

The presently known amines have, in general, the disadvantage that they may be emitted from the polyurethane (PU) material, usually being foams such as flexible foams, as VOC's and/or odorous species, or cause fogging.

It is an object of the present invention to provide amines suitable as PU-catalyst.

According to a first aspect of the present invention, an amine is provided, which amine complies with formula

$(CH_3)_2NCH_2CH_2OCH_2CH_2CH_2N(R1)(R2)$ wherein R1 is selected from $(CH_3)_2NCH_2CH_2OCH_2CH_2CH_2-$ and R2 is selected from the group consisting of H—, $CH_3(C_nH_{2n})-$, $HO(C_mH_{2m})-$ and $(CH_3)_2NCH_2CH_2OCH_2CH_2CH_2-$, n being an integer in the range of 0 to 5, m being an integer in the range of 2 to 4.

$CH_3(C_nH_{2n})-$, for which n may be 0, 1, 2, 3, 4 or 5 represents a linear or branches alkyl group.

$HO(C_mH_{2m})-$, for which m may be 2, 3, or 4 represents a linear or branches alkyihydroxide group.

According to some embodiments of the present invention, R2 may be selected from the group consisting of H—, $CH_3-$ and $(CH_3)_2NCH_2CH_2OCH_2CH_2CH_2-$.

According to some embodiments of the present invention, R1 is selected from $(CH_3)_2NCH_2CH_2OCH_2CH_2CH_2-$ and R2 is selected from the group consisting of H—, $CH_3-$ and $(CH_3)_2NCH_2CH_2OCH_2CH_2CH_2-$.

According to some embodiments of the present invention, R1 may be $(CH_3)_2NCH_2CH_2OCH_2CH_2CH_2-$, R2 being H.

This component is also referred to as bis(dimethylaminoethoxypropyl)amine.

According to some embodiments of the present invention, R1 may be $(CH_3)_2NCH_2CH_2OCH_2CH_2CH_2-$, R2 being $CH_3-$.

This component is also referred to as bis(dimethylaminoethoxypropyl) methyl amine.

According to some embodiments of the present invention, R1 may be $(CH_3)_2NCH_2CH_2OCH_2CH_2CH_2-$, R2 being $HO(C_mH_{2m})-$, m being an integer in the range of 2 to 4.

These amines may be obtained by reacting bis(dimethylaminoethoxypropyl)amine with ethylene oxide, propylene oxide or butylenes oxide.

According to some embodiments of the present invention, R1 may be $(CH_3)_2NCH_2CH_2OCH_2CH_2CH_2-$, R2 being $(CH_3)_2NCH_2CH_2OCH_2CH_2CH_2-$.

This component is also referred to as tris(dimethylaminoethoxypropyl)amine

According to a second aspect of the present invention, a composition comprising one or more amines according to the first aspect of the invention is provided.

The amine according to the first aspect of the present invention, was found to be suitable as a catalyst in a polyurethane reaction composition. In particular it predominantly catalyses the blowing reaction which consists of an isocyanate such as TDI (toluene diisocyanate) or MDI (methylene diisocyanate) reacting with water to form carbon dioxide (the blowing gas) and a disubstituted urea. These catalysts may also catalyze the gelling reaction, which consists of the isocyanate reacting with the polyol or any other active hydrogen compound to form a polyurethane polymer.

According to a third aspect of the present invention, a composition according to the second aspect of the invention is used as catalyst in a polyurethane reaction mixture comprising said composition, at least one component comprising an isocyanate group and at least one component comprising an isocyanate reactive group.

Preferably the amines according to the first aspect of the present invention is present in the polyurethane reaction mixture in an amount of 0.01% w to 10% w. An amount of 0.03% to 2.0% w is more preferred. These weights are based on a percentage of total formulation weight, i.e the weight of all ingredients in the reaction mixture, including the isocyanate component, the isocyanate reactive component, the catalyst according to the first aspect of the invention, and all other additives used in the reaction mixture.

The at least one component comprising an isocyanate group may be a component being a diisocyanate of a polyisocyanate component. Preferably the at least one component comprising an isocyanate group is methyldiphenyldiisocyanate (MDI) or toluene diisocyanate (TDI). The MDI or TDI may be provided in their normal composition of a mixture f different isocyanate species. As well known in the art.

The at least one component comprising an isocyanate reactive group may be polyalcohols (also referred to as polyols), polyamines or any other component well known in the art.

The polyurethane reaction mixture, once reacted, may provide a polyurethane product such as a flexible, semi-rigid or rigid polyurethane foam, in particular polyurethane flexible molded foam, flexible slabstock foam and semi-flexible foam, but also polyurea elastomer or two component coating, and polyurethane elastomer.

The preferred use of the amines according to the third aspect of the present invention is the provision of a catalyst to a polyurethane reaction mixture for making flexible or semi-rigid polyurethane foam.

When the amines according to the invention, used as catalysts, are secondary amines or (R2 being hydrogen) or tertiary amines (R2 being $HO(C_mH_{2m})-$, m being an integer in the range of 2 to 4), the amines are reactive catalysts, and will be bond in the polyurethane product. This, combined with their increased molecular weight and reduced volatility (due to a lowered vapor pressure) over presently used alternative catalysts, results in a reduction of the VOC's which may be emitted from the foam made.

When the amines used as catalysts are tertiary amines (R2 not being hydrogen or $HO(C_mH_{2m})-$, m being an integer in the range of 2 to 4) the amines are not reactive catalysts, and hence will not be bond in the polyurethane product. However, their increased molecular weight and reduced volatility (due to a lowered vapor pressure) over presently used alternative catalysts, are sufficient to cause a reduction of the VOC's which may be emitted from the foam made.

The amine emission reduction results in offensive odor reduction since amines often have foul, fish-like odors which are both repugnant and can have adverse health effects. The reactive and high molecular weight amines have these advantages over conventionally used amine blowing catalysts which are nonreactive, volatile, low molecular weight amines such as Bisdimethylaminoethylether.

According to a fourth aspect of the present invention, a process for making at least one amine according to the first aspect of the present invention is provided. The process comprises
  a) Reacting $(CH_3)_2NCH_2CH_2OH$ with acrylonitrile thereby providing a first mixture comprising $(CH_3)_2NCH_2CH_2OH$, acrylonitrile and $(CH_3)_2NCH_2CH_2OCH_2CH_2CN$;
  b) Catalytically hydrogenation of said first mixture to provide a second mixture comprising
  $(CH_3)_2NCH_2CH_2OH$;
  $(CH_3)_2NCH_2CH_2OCH_2CH_2CH_2NH_2$;
  $((CH_3)_2NCH_2CH_2OCH_2CH_2CH_2)_2NH$ and
  $((CH_3)_2NCH_2CH_2OCH_2CH_2CH_2)_3N$;
  c) Separation of said components from said second mixture by distillation.

According to some embodiments of the invention, the at least one amine is $((CH_3)_2NCH_2CH_2OCH_2CH_2CH_2)_2NCH_3$, said process further comprising the reaction of said separated $((CH_3)_2NCH_2CH_2OCH_2CH_2CH_2)_2NH$ with formaldehyde and hydrogen in thereby providing a third mixture comprising $((CH_3)_2NCH_2CH_2OCH_2CH_2CH_2)_2NCH_3$.

This reaction with formaldehyde and hydrogen usually is applied in the presence of a solvent, such as methanol. Therefore, formaldehyde can be used as a mixture of formaldehyde and said solvent, e.g. methanol or n-buthanol.

Two separate reaction steps may be used, first reacting $((CH_3)_2NCH_2CH_2OCH_2CH_2CH_2)_2NH$ with formaldehyde to provide an intermediate. This intermediate is thereafter hydrogenated with hydrogen, typically over a suitable hydrogenation catalyst such as a Nickel-based catalyst.

By distillation and/or evaporation, $((CH_3)_2NCH_2CH_2OCH_2CH_2CH_2)_2NCH_3$ can be separated from this third mixture.

The reaction of $(CH_3)_2NCH_2CH_2OH$, also known as dimethylethanolamine or DMEA with acrylonitrile is preferably preformed in the presence of a catalysing medium, such as sodiummethylate.

Preferably $(CH_3)_2NCH_2CH_2OH$ is reacted with acrylonitrile while mixing, in order to prevent the acrylonitrile to polymerise.

It is preferred to add acrylonitrile to the entire mass of the DMEA solution used in the reaction. DMEA, at room temperature being a liquid, and adding acrylonitrile to this excess of DMEA prevent the polymerization of acrylonitrile to polyacrylonitrile.

NaOMe is also referred to as sodium methylate or sodium methoxide. The reaction temperature can be 0 to 80 deg C., the pressure can be from ambient to 10 bar and preferably the temperature is from 25 to 55 C. and pressure is below 5 bar. The reaction typically takes 2 to 8 hours to complete.

As such a first mixture is provided. This first mixture typically comprises 0 to 40% w $(CH_3)_2NCH_2CH_2OH$ (dimethylethanolamine), 0-5% w acrylonitrile and 60 to 100% w DMEA-Nitrile $(CH_3)_2NCH_2CH_2O-CH2-CH2-CN$. The preferred mixture comprise 0 to 10% w $(CH_3)_2NCH_2CH_2OH$ (dimethylethanolamine), 0-1% w acrylonitrile and 90 to 100% w DMEA-Nitrile $(CH_3)_2NCH_2CH_2O-CH2-CH2-CN$.

Catalytically hydrogenation of this first mixture is used to provide a second mixture.

A typical hydrogenation catalyst may be used such as nickel-based catalyst or precious metal catalyst. The temperature of the process according to the invention may be 50 deg C to 180 deg C. and pressure is from 3 bar to 300 bar, the preferred temperature is from 70 C to 140 C. and pressure from 10 bar to 200 bar depending on the catalyst of choice. Hydrogen is added for reaction and also maintains the catalyst integrity. The typical hydrogen amount is 2 to 6 mol/mol DMEA-nitrile. Ammonia can be added to affect the reaction selectivity and activity. The reaction can be batch or continuous.

As such a second mixture is provided. This second mixture typically comprises 20 to 90% w $((CH_3)_2NCH_2CH_2OCH_2CH_2CH_2)_2NH$, 0 to 40% w $(CH_3)_2NCH_2CH_2OH$, 20 to 90% w $(CH_3)_2NCH_2CH_2OCH_2CH_2CH_2NH_2$ and 20 to 60% w $((CH_3)_2NCH_2CH_2OCH_2CH_2CH_2)_3N$. Preferably the composition is 20 to 50% w $((CH_3)_2NCH_2CH_2OCH_2CH_2CH_2)_2NH$, 0 to 10% w $(CH_3)_2NCH_2CH_2OH$, 20 to 50% w $(CH_3)_2NCH_2CH_2OCH_2CH_2CH_2NH_2$ and 0 to 50% w $((CH_3)_2NCH_2CH_2OCH_2CH_2CH_2)_3N$ By distillation, as well known to the skilled person, the components can be separated one from the other. It is understood that the obtained components may still include some of the other components as impurities.

After distillation, the $((CH_3)_2NCH_2CH_2OCH_2CH_2CH_2)_2NH-$ fraction may comprise 80 to 100% w $((CH_3)_2NCH_2CH_2OCH_2CH_2CH_2)_2NH$, 0 to 10% w $(CH_3)_2NCH_2CH_2OCH_2CH_2CH_2NH_2$ and other impurity. This fraction may contain 90 to 100% w $((CH_3)_2NCH_2CH_2OCH_2CH_2CH_2)_2NH$, 0 to 2% w $(CH_3)_2NCH_2CH_2OCH_2CH_2CH_2NH_2$ and other impurities.

The separated $((CH_3)_2NCH_2CH_2OCH_2CH_2CH_2)_2NH$ may be reacted with formaldehyde in the presence of a solvent, e.g. methanol and/or water, after which it is hydrogenated, typically over a hydrogenation catalyst, to provide a third mixture comprising $((CH_3)_2NCH_2CH_2OCH_2CH_2CH_2)_2NCH_3$.

As such a third mixture is provided. This third mixture typically may comprise 80 to 100% w $((CH_3)_2NCH_2CH_2OCH_2CH_2CH_2)_2NCH_3$ and 0 to 10% w $(CH_3)_2NCH_2CH_2OCH_2CH_2CH_2N(CH_3)_2$, 0 to 5% w $((CH_3)_2NCH_2CH_2OCH_2CH_2CH_2)_2NCH2CH2CH_3$ and other impurities The typical mixture may comprise 90 to 100% w $((CH_3)NCH_2CH_2OCH_2CH_2CH_2)_2)NCH_3$.

By separation, such as distillation, as well known to the skilled person, $((CH_3)_2NCH_2CH_2OCH_2CH_2CH_2)_2NCH_3$ can be separated from the third mixture. It is understood that the obtained $((CH_3)_2NCH_2CH_2OCH_2CH_2CH_2)_2NCH_3$ may still include some of the other components as impurities.

The impurities can include 0 to 5% w $(CH_3)_2NCH_2CH_2OCH_2CH_2CH_2N(CH_3)_2$, 0 to 5% w $((CH_3)_2NCH_2CH_2OCH_2CH_2CH_2)_3N$, 0 to 1% w $(CH_3)_2NCH_2CH_2OH$ and 0 to 10% $((CH_3)_2NCH_2CH_2OCH_2CH_2CH_2)_3N$ and 0 to 10% w $((CH_3)_2NCH_2CH_2OCH_2CH_2CH_2)_2NCH2CH2CH_3$. The typical impurities are 0 to 1% w $(CH_3)_2NCH_2CH_2OCH_2CH_2CH_2N(CH_3)_2$, 0 to 5% w $((CH_3)_2NCH_2CH_2OCH_2CH_2CH_2)_3N$ and 0 to 5% w $((CH_3)_2NCH_2CH_2OCH_2CH_2CH_2)_2NCH2CH2CH_3$.

The independent and dependent claims set out particular and preferred features of the invention. Features from the dependent claims may be combined with features of the independent or other dependent claims as appropriate.

The above and other characteristics, features and advantages of the present invention will become apparent from the following detailed description which illustrate, by way of example, the principles of the invention. This description is given for the sake of example only, without limiting the scope of the invention.

The present invention will be described with respect to particular embodiments.

It is to be noticed that the term "comprising", used in the claims, should not be interpreted as being restricted to the means listed thereafter; it does not exclude other elements or steps. It is thus to be interpreted as specifying the presence of the stated features, steps or components as referred to, but does not preclude the presence or addition of one or more other features, steps or components, or groups thereof. Thus, the scope of the expression "a device comprising means A and B" should not be limited to devices consisting only of components A and B. It means that with respect to the present invention, the only relevant components of the device are A and B.

Throughout this specification, reference to "one embodiment" or "an embodiment" are made. Such references indicate that a particular feature, described in relation to the embodiment is included in at least one embodiment of the present invention. Thus, appearances of the phrases "in one embodiment" or "in an embodiment" in various places throughout this specification are not necessarily all referring to the same embodiment, though they could. Furthermore, the particular features or characteristics may be combined in any suitable manner in one or more embodiments, as would be apparent to one of ordinary skill in the art.

The following terms are provided solely to aid in the understanding of the invention. Unless otherwise mentioned, when reference is made to % w, w % or weight percentage of a component in a composition, reference is made to the weight of said component over the total weight of said composition, expressed as percentage, at that moment in time or in the series of production steps.

Following names refer to following components with formula:

dimethylethanol amine (DMEA): $(CH_3)_2NCH_2CH_2OH$
dimethylaminoethoxypropylamine: $(CH_3)_2NCH_2CH_2OCH_2CH_2CH_2NH_2$
dimethylaminoethoxypropionitrile (DMEN): $(CH_3)_2NCH_2CH_2OCH_2CH_2CN$
bis(dimethylaminoethoxypropyl)amine: $((CH_3)_2NCH_2CH_2OCH_2CH_2CH_2)_2NH$
tris(dimethylaminoethoxypropyl)amine: $((CH_3)_2NCH_2CH_2OCH_2CH_2CH_2)_3N$
bis(dimethylaminoethoxypropyl) methyl amine:

$((CH_3)_2NCH_2CH_2OCH_2CH_2CH_2)_2NCH_3$

A.—Process to Provide Amines According to the Invention 9.75 kg (21.1 lbs) dimethylethanol amine (DMEA) and 7.5 gram 25% w sodium methylate mixtures were charged into the 4 gallon kettle; 4.85 kg (10.7 lbs) acrylonitrile are fed to the mixture over a 2 hours period, the temperature of the mixture is maintained below 60° C. by jacket cooling. The final product contain 15% w DMEA and 85% w dimethylaminoethoxypropionitrile (DMEN) and 0.2% acrylonitrile. The sodium cation in the mixture was removed using cation ion-exchanger resin.

A tubular reactor filled with 150 cc of catalyst was used. The catalyst used about 75% w Nickel and about 11% w copper. The product from above was fed at a rate of 60 g/hr and hydrogen at 60 l/hr. The reactor pressure was 138.9 bar (2000 psig) and hot spot was 110° C. The effluent came out of the reactor contained about 53% w bis(dimethylaminoethoxypropyl)amine, 24% w dimethylaminoethoxypropylamine, 15% w DMEA, 3% w tris(dimethylaminoethoxypropylamine and some light components. No DMEN was detected in GC. These mixtures could be easily separated using distillation column.

In this experiment, a tubular reactor filed with 85 cc of catalyst (same catalyst as above) was used. Bis(dimethylaminoethoxypropyl)amine (feed 1) was fed at a rate of 40 g/hr and methyl formacel (37% w formaldehyde, 15% w methanol and 48% w water) (feed 2) was fed at 25 g/hr. Feed 1 and feed 2 were pumped through a 10-15 ft stainless coil before mixing with Hydrogen. The hydrogen was fed at 10 l/hr. The reactor pressure was 138.9 bar (2000 psig) and hot spot was 115° C. As the effluent came out of the reactor, the excess formaldehyde was allowed to evaporate. Methanol and water were then removed from the mixture using distillation column. The final product contains 94.6% w bis(dimethylaminoethoxypropyl) methyl amine and tertiary amine is 10.4 meq/g

B.—Use of Amines According to the Invention as Catalyst

Several amines as prepared above, are used as part of a catalyst system for producing a PU material, i.e. a flexible polyurethane foam.

Following references are made;
Catalyst A: bis(dimethylaminoethoxypropyl)amine
Catalyst B: dimethylaminoethoxypropylamine
Catalyst C: tris(dimethylaminoethoxypropyl)amine
Catalyst D: bis(dimethylaminoethoxypropyl) methyl amine From these catalysts the 20° C. Vapor Pressure, expressed in mm Hg, was measured and is reported in table I.

TABLE I

| Catalyst component | 20° C. Vapor Pressure mm Hg |
|---|---|
| Bis(dimethylaminoethyl)ether | 0.247 |
| Catalyst B | 0.186 |
| Catalyst A | 3.48E−06 |
| Catalyst D | 7.10E−05 |

Vapor pressures were measured at Washburn ebulliometer (dynamic method) as detailed in EPA Product Properties Test Guidelines: OPPTS 830.7950 Vapor Pressure [EPA 712-C-96-043].

As can be seen the catalysts of this invention have substantially lower vapor pressures as compared to a known catalyst Bis(dimethylaminoethyl)ether, available from Huntsman International LLC as JEFFCAT ZF-20 and compared to state of the art reactive amine catalysts (e.g. monomer dimethylaminoethoxypropylamine).

Polyurethane reactive mixtures as set out in Table II were prepared and reacted.
VORANOL 3136 is a nominal 3100 molecular weight heteropolymer triol polyol made by The Dow Chemical Co,
VORANOL 3010 is a glycerine initiated, nominal 3000 molecular weight heteropolymer triol polyol made by The Dow Chemical Co.
Silicone L-620 is a silicone surfactant used in polyurethane flexible slabstock foams made by Momentive Performance Materials
KOSMOS 15p is 50% stannous octoate dissolved in mineral oil made by Evonik Goldschmidt GmbH.

TABLE II

| Compound | Ex 1 | Ex 2 | Ex 3 | Ex 4 | Ex 5 |
|---|---|---|---|---|---|
| VORNAOL 3136 (ppw) | | 100 | 100 | 100 | 100 |
| VORANOL 3010 (ppw) | 100 | | | | |
| Water (ppw) | 2.8 | 2.8 | 2.8 | 2.8 | 2.8 |
| Silicone L-620 (ppw) | 1.0 | 1.0 | 1.0 | 1.0 | 1.0 |
| Catalyst A (ppw) | 0.30 | | | | |
| Catalyst B (ppw) | | 0.42 | | | |
| Catalyst C (ppw) | | | 0.30 | | |
| Catalyst D (ppw) | | | | 0.30 | |
| Bis(dimethylamino-ethyl)ether (ppw) | | | | | 0.12 |
| KOSMOS 15p (ppw) | 0.30 | 0.30 | 0.30 | 0.30 | 0.30 |
| Toluene diisocyanate (ppw) | 39.12 | 39.12 | 39.12 | 39.12 | 39.12 |
| VDA-278 Foam Emissions Test | | | | | |
| VOC ppm | 78.2 | 47 | | 43.5 | 1200 |
| FOG ppm | 86.2 | 52 | | 39.8 | 1770 |

All components are expressed as parts per weight (ppw) VDA-278 foam emission test refers to the DaimlerChrysler PB VWL 709 VOC and FOG (VDA 278).

The VOC portion of this test consists of placing a small foam sample in a tube and heating it for 30 minutes at 90° C. and inert gas extraction is used to remove all foam volatiles. The volatile emissions are trapped and condensed in a cryogenic trap at −150° C. The trapped residue is then heated to 120° C. and injected into a gas chromatograph to measure total emissions content (VOC). Total emissions are reported as micrograms of emissions as toluene/gram of foam sample. The FOG portion of the test is done exactly like the VOC test except the small foam sample is heated to 120° C. for 1.5 hours and the gas chromatograph emissions content is reported as micrograms of emissions as hexadecane/gram of foam sample.

As can be seen the catalyst of this invention have much lower VOC and FOG values as compared to Bis(dimethylaminoethyl)ether. Even compared to reactive amine catalyst components such as the catalyst component B being dimethylaminoethoxypropylamine, the catalyst components according to the invention which are non-reactive catalyst components such as catalyst component D being bis(dimethylaminoethoxypropyl) methyl amine give surprisingly good FOG and VOC emission values due to their low vapor pressure.

Further polyurethane reactive mixtures as set out in Table III were prepared and reacted to provide a polyurethane flexible foam.

KOSMOS 15p is 50% stannous octoate dissolved in mineral oil made by Evonik Goldschmidt GmbH. Kosmos 15n (referred to in #10 below) is 50% stannous octoate dissolved in nonylphenol.

TABLE III

| Compound | Ex 6 | Ex 7 | Ex 8 |
|---|---|---|---|
| VORANOL 3010 (ppw) | 100 | | 100 |
| VORNAL 3136 (ppw) | | 100 | |
| Water (ppw) | 2.8 | 2.8 | 2.8 |
| Silicone L-620 (ppw) | 1.0 | 1.0 | 1.0 |
| Catalyst A (ppw) | 0.30 | | |
| Catalyst C (ppw) | | 0.30 | |
| Catalyst D (ppw) | | | 0.30 |
| KOSMOS 15P (ppw) | 0.12 | 0.30 | |
| KOSMOA 15N (ppw) | | | 0.30 |
| Toluene diisocyanate | 39.12 | 39.12 | 39.12 |
| Rise time (sec) | 143 | 138 | 147 |

To match the rise profile of the foam less moles of the catalyst according to the invention (dimer and trimer amine catalyst) are required (corresponding to catalysts components A, C and D) compared to the monomer catalyst B to produce the same rise profile. To get the same rise profile 0.4 grams (0.0039 moles) of catalyst B are required while only 0.3 grams (0.001 moles) of catalyst A, C and D are required. This result is surprising because if you base the calculation of amount of catalyst required on available dimethyl amine groups, catalyst B has only 1 dimethyl amine group while catalyst C (trimer) has 3 dimethyl amine groups. For catalyst B hence the equivalent of dimethyl amine group used to generate the profile is 0.0039*1=0.0039 equivalent of dimethyl amine groups. For catalyst C (the trimer), the dimethyl amine equivalents are 0.001*3=0.003 dimethyl amine equivalents. Less dimethyl amine equivalents are hence used to catalyze the reaction with the trimer catalyst compared to the monomer catalyst. This surprisingly makes the dimer and trimer amine catalysts according to the invention more potent catalysts.

It is to be understood that although preferred embodiments and/or materials have been discussed for providing embodiments according to the present invention, various modifications or changes may be made without departing from the scope and spirit of this invention.

The invention claimed is:

1. An amine having the formula

$(CH_3)_2NCH_2CH_2OCH_2CH_2CH_2N(R1)(R2)$ wherein R1 is $(CH_3)_2NCH_2CH_2OCH_2CH_2CH_2$— and R2 is $HO(C_mH_{2m})$— and wherein m is an integer in the range of 2 to 4.

* * * * *